(12) United States Patent
Loos

(10) Patent No.: US 11,185,661 B1
(45) Date of Patent: Nov. 30, 2021

(54) WEIGHTED BLANKET

(71) Applicant: Proper Pillow, Carlsbad, CA (US)

(72) Inventor: Richard Arland Loos, Encinitas, CA (US)

( * ) Notice: Subject to any disclaimer, the term of this patent is extended or adjusted under 35 U.S.C. 154(b) by 0 days.

(21) Appl. No.: 16/740,370

(22) Filed: Jan. 10, 2020

Related U.S. Application Data

(60) Provisional application No. 62/791,019, filed on Jan. 10, 2019.

(51) Int. Cl.
*A61M 21/02* (2006.01)
*A47G 9/02* (2006.01)
*A61M 21/00* (2006.01)

(52) U.S. Cl.
CPC ........... *A61M 21/02* (2013.01); *A47G 9/0223* (2013.01); *A61M 2021/0022* (2013.01)

(58) Field of Classification Search
CPC ................ A47G 9/0223; A61M 21/02; A61M 2021/0022
See application file for complete search history.

(56) References Cited

U.S. PATENT DOCUMENTS

| | | | |
|---|---|---|---|
| 2009/0100568 A1* | 4/2009 | Judd | A61H 7/001 2/95 |
| 2011/0047698 A1* | 3/2011 | Parker | A47G 9/0207 5/502 |
| 2011/0250331 A1* | 10/2011 | Murray | B32B 7/05 426/418 |
| 2012/0186015 A1* | 7/2012 | Shattuck | A47G 9/0261 5/485 |
| 2015/0074906 A1* | 3/2015 | Hiatt | A47C 31/105 5/484 |
| 2018/0035832 A1* | 2/2018 | Ureten | A61M 21/02 |
| 2019/0021525 A1* | 1/2019 | Hamm | B32B 3/06 |
| 2020/0179641 A1* | 6/2020 | Russin, Sr. | B32B 7/022 |
| 2020/0236907 A1* | 7/2020 | Nilsson | A01K 13/008 |

* cited by examiner

*Primary Examiner* — David R Hare
*Assistant Examiner* — Alexis Felix Lopez
(74) *Attorney, Agent, or Firm* — Michael D. Eisenberg

(57) ABSTRACT

A weighted blanket, comprising: a lower layer of blanket material; a perforated layer having a plurality of similarly shaped and sized apertures, each aperture defining a cell, the perforated layer being disposed above the lower layer; a plurality of beads distributed over the lower layer; an upper layer of blanket material disposed above the lower layer of blanket material, such that the lower level and the upper level sandwich the perforated layer and the bead. The lower layer, the upper layer, and the perforated layer are sewn together in a sewing pattern that divides the weighted blanket into a plurality of substantially equal sections, such that beads in any of the sections are prevented from crossing into any other one of the sections.

16 Claims, 6 Drawing Sheets

700

WEIGHTED BLANKET

CROSS-REFERENCES TO RELATED APPLICATIONS

This application claims priority from U.S. Provisional Application Ser. No. 62/791,019 filed on Jan. 10, 2019, which is hereby incorporated herein by reference in the respective in its entirety.

TECHNICAL FIELD

The present invention relates to a weighted blanket for deep pressure therapy purposes.

BACKGROUND OF THE INVENTION

There are various types of blankets on the market today. Yet, there are several unresolved issues with the structure and use of many blankets. Most blankets do not provide enough warmth due to their structure, lack of layers, or thin material. Further, a blanket is generally not very rigid and moves very easily off of a person's body or bed, decreasing the blanket's efficiency to provide warmth and heat.

In the art, some blankets are known to include micro beads within a sandwich of fiberfill to add to the weight of the blanket.

BRIEF SUMMARY OF EMBODIMENTS OF THE INVENTION

While the blanket with micro beads are indeed heavier, the beads fall to the lowest point of the blanket due to gravity, and pool therein. This pooling effect is undesirable, as the distribution of the weight of the blanket is altered during the blanket's use and becomes concentrated in one or more pockets. Thus, during use, even a weighted blanket is no longer homogenously weighted over the user's body, decreasing the comfort provided by the blanket and not preventing the falling of the blanket while the user sleeps.

The present invention addresses these issues, by providing a novel weighted blanket and a method of manufacturing the weighted blanket. The weighted blanked of the present invention comprises several layers of blanket material, to increase the weight of the blanket. A perforated layer sandwiched between the layers of blanket material helps to hold beads in place and enables a substantially homogeneous distribution of weight throughout the blanket. In some embodiments, the blanket has an outer surface fully made out of cotton breathable fabric, amenable for human body temperature. The beads may be made of silica or lead-free glass, which are known to be non-toxic, hypoallergenic, and odorless. The layers of blanket material may be polyfill layers, which include polyester to prevent tears and leakage of the beads.

Therefore, an aspect of some embodiments of the present invention relates to a weighted blanket, comprising: a lower layer of blanket material; a perforated layer having a plurality of similarly shaped and sized apertures, each aperture defining a cell, the perforated layer being disposed above the lower layer; a plurality of beads distributed over the lower layer; an upper layer of blanket material disposed above the lower layer of blanket material, such that the lower level and the upper level sandwich the perforated layer and the beads; wherein the lower layer, the upper layer, and the perforated layer are sewn together in a sewing pattern that divides the weighted blanket into a plurality of substantially equal sections, such that beads in any of the sections are prevented from crossing into any other one of the sections; and wherein prior to the sewing of the lower layer, the upper layer, and the perforated layer, the beads are distributed substantially uniformly over the lower layer of blanket material such that each cell contains substantially a same number of beads and the perforated layer prevents the beads from leaving the respective cell, thereby ensuring that once the lower layer, the upper layer, and the perforated layer are sewn together, each section contains substantially a same amount of beads, thereby ensuring a substantially uniform distribution of beads over the blanket.

The blanket may also have a lattice matrix disposed parallel to the layers of blanket material and joined to at least one of the layers of blanket material, the lattice matrix comprising a pattern of shaped holes alternating with similarly shaped and sized units of fabric, the fabric being at least semi-rigid, such that lattice matrix is configured to be flexible while retaining a shape of the blanket.

The blanket may also have at least one of: an upper padding layer disposed above the upper layer of blanket material, and a lower padding layer is disposed below the lower later of blanket material.

The blanket may also have at least one tie loop joined to at least one edge of the upper padding layer or the lower padding layer and being configured to attach to an external structure.

The blanket may be as described above with the sections being rectangular or square.

In a variant of the blanket, the upper padding layer and/or the lower padding layer comprises preshrunk cotton fabric.

In another variant of the blanket, the lower layer of blanket material and/or the upper layer of blanket material comprises polyfill.

In a further variant of the blanket, the cells of the perforated layer are honeycomb shaped.

In still another variant of the blanket, the perforated layer comprises elastic fabric.

In a variant, a method for manufacturing a blanket comprises: providing a lower layer of blanket material as a foundation; laying the lower layer of blanket material horizontally; placing a perforated layer on the lower layer, the perforated layer having a plurality of similarly shaped and sized apertures, each aperture defining a cell, above the lower layer; spreading a plurality of beads substantially uniformly on a top of the lower layer with the cells above the lower blanket layer, such that each cell contains substantially a same amount of beads, the perforated layer preventing the beads from leaving the respective cells; placing an upper layer of blanket material on a top of the lower layer such that the lower layer and the upper layer sandwich the perforated layer and the beads; and sewing the lower layer, upper layer, and the perforated layer together according to a sewing pattern which divides the blanket into a plurality of substantially equal sections, such that each section contains substantially a same amount of beads and that the beads in any of the sections are prevented from crossing between sections, thereby maintaining a substantially uniform distribution of the beads over the blanket.

In a variant, the method further comprises joining a lattice matrix to at least one of the upper layer and the lower layer, such that the lattice matrix is disposed parallel to the upper layer and the lower layer, the lattice matrix having a pattern of a shaped holes alternating with similarly shaped and sized units of fabric, the fabric being at least semi-rigid, such that lattice matrix is configured to be flexible while retaining a shape of the blanket.

In another variant, the method comprises at least one of: joining an upper padding layer to a top of the upper layer of blanket material; and joining a lower padding layer to a bottom of the lower layer of blanket material.

In a further variant, the method comprises joining at least one tie loop to at least one edge of the upper padding layer or of the lower padding layer, the at least one tie loop being configured to attach to an external structure.

In yet another variant of the method, the substantially equal sections are square or rectangular.

In still a further variant of the method, the upper padding layer and/or the lower padding layer comprise preshrunk cotton fabric.

In a variant of the method, the lower layer of blanket material and/or the upper layer of blanket material comprise polyfill.

In another variant of the method, the cells of the perforated layer that are honeycomb shaped.

In a further variant of the method, the perforated layer comprises elastic fabric.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

Figure 1:
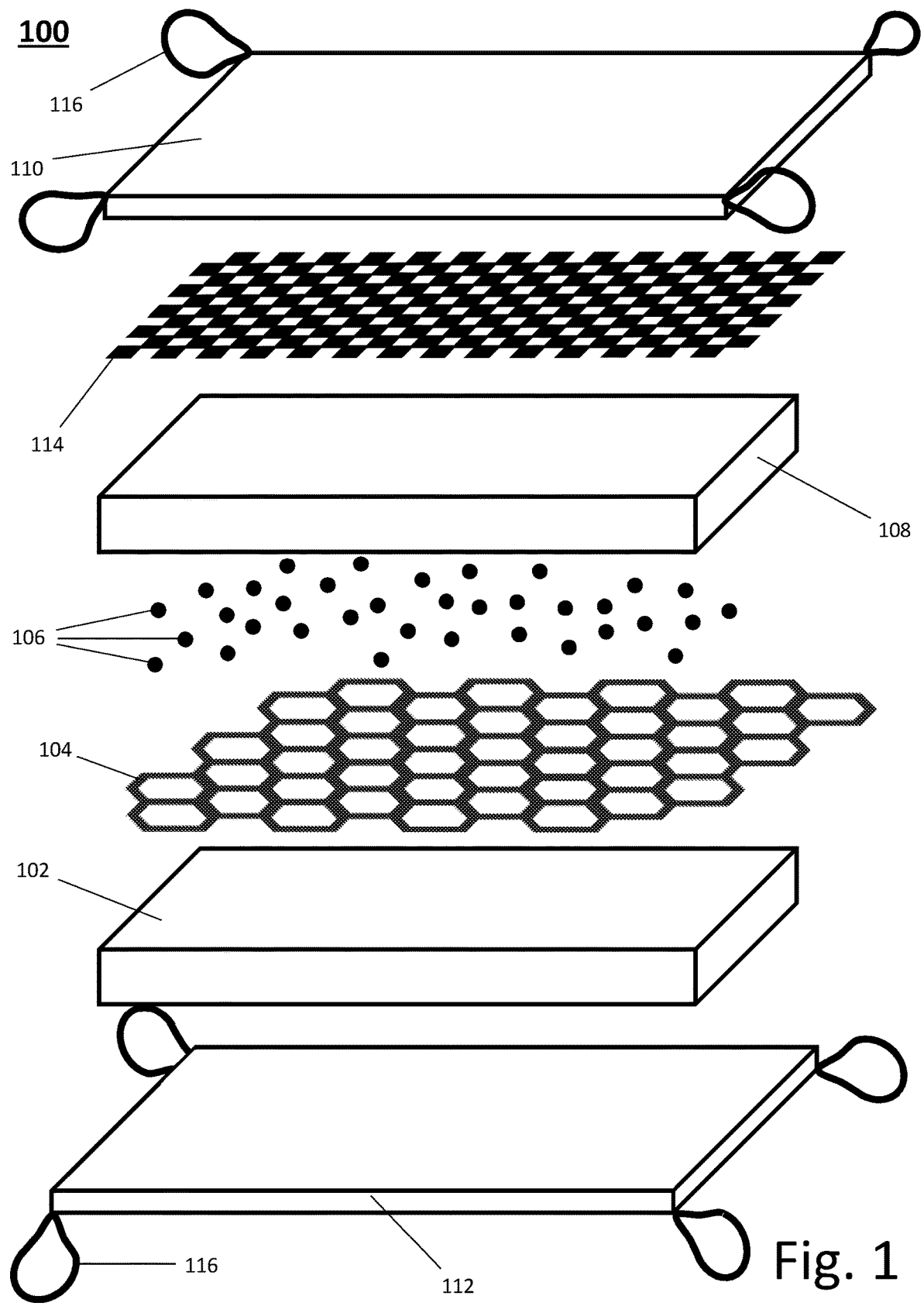
FIG. 1 is an exploded view of a weighted blanket, according to some embodiments of the present invention.

Referring now to the drawings, FIG. 1 is an exploded view of a weighted blanket 100, according to some embodiments of the present invention.

The weighted blanket 100 comprises a lower layer 102 of blanket material, a perforated layer 104, a plurality of beads 106, and an upper layer 108. The lower layer of 102 and the upper layer 108 are configured for sandwiching the perforated layer 104 and the beads 106. The lower layer 102 and the upper layer 108 are made of compliant material, for the user's comfort. The lower layer 102 and the upper layer 108 do not allow the beads 106 to pass therethough. In some embodiments of the present invention, at least one of the lower layer 102 and the upper later 108 includes polyester, such as polyfill, to prevent tears and leakage of the beads through the layer of blanket material.

The perforated layer 104 is joined to the top of the lower layer 102, and has a plurality of similarly shaped and sized apertures 104a, each aperture defining a cell. A plurality of beads 106 is distributed over the lower layer 102 on the perforated layer 104. As will be explained further below, with reference to FIGS. 2 and 3, the perforated layer 104 helps distribute the beads 106 on the lower layer 102 in a uniform manner and maintain the uniform distribution until the lower layer 102, perforated layer 104, and upper layer 108 are sewn together.

The lower layer 102, the upper layer 108, and the perforated layer 104 are sewn together in a sewing pattern that divides the weighted blanket 100 into a plurality of substantially equal sections, such that beads 106 in any of the sections are prevented from crossing into any other one of the sections. Because the beads are homogeneously distributed over the lower layer 102, prior to the sewing, the beads are still homogeneously distributed over the blanket 102 after the sewing, such that each section of the blanket includes approximately the same number of beads.

In some embodiments of the present invention, an upper padding layer 110 is disposed above the upper layer 108 of blanket material, and a lower padding layer 112 is disposed below the lower layer 102 of blanket material. The padding layers may include soft materials to enhance the comfort of the user. The padding layers may include heat retaining material, to enhance the heat retaining properties of the blanket. A material that is both soft and heat retaining may be, for example, preshrunk cotton.

In a variant, at least one tie loop 116 is joined to at least one edge of the upper padding layer 110 or the lower padding layer 112. The tie loop 116 is configured to attach to an external structure, such as a bed post, to retain the blanket 100 on the bed, even as a user sleeps and moves under the blanket 100.

According to some embodiments of the present invention, the blanket 100 includes a lattice matrix 114 disposed parallel to the layers of blanket material (102, 108) and joined to at least one of the layers of blanket material. The lattice matrix 114 includes a pattern of shaped holes alternating with similarly shaped and sized units of fabric, the fabric being at least semi-rigid, such that the lattice matrix 114 is configured to be flexible while retaining a shape of the blanket 100.

Figure 2:
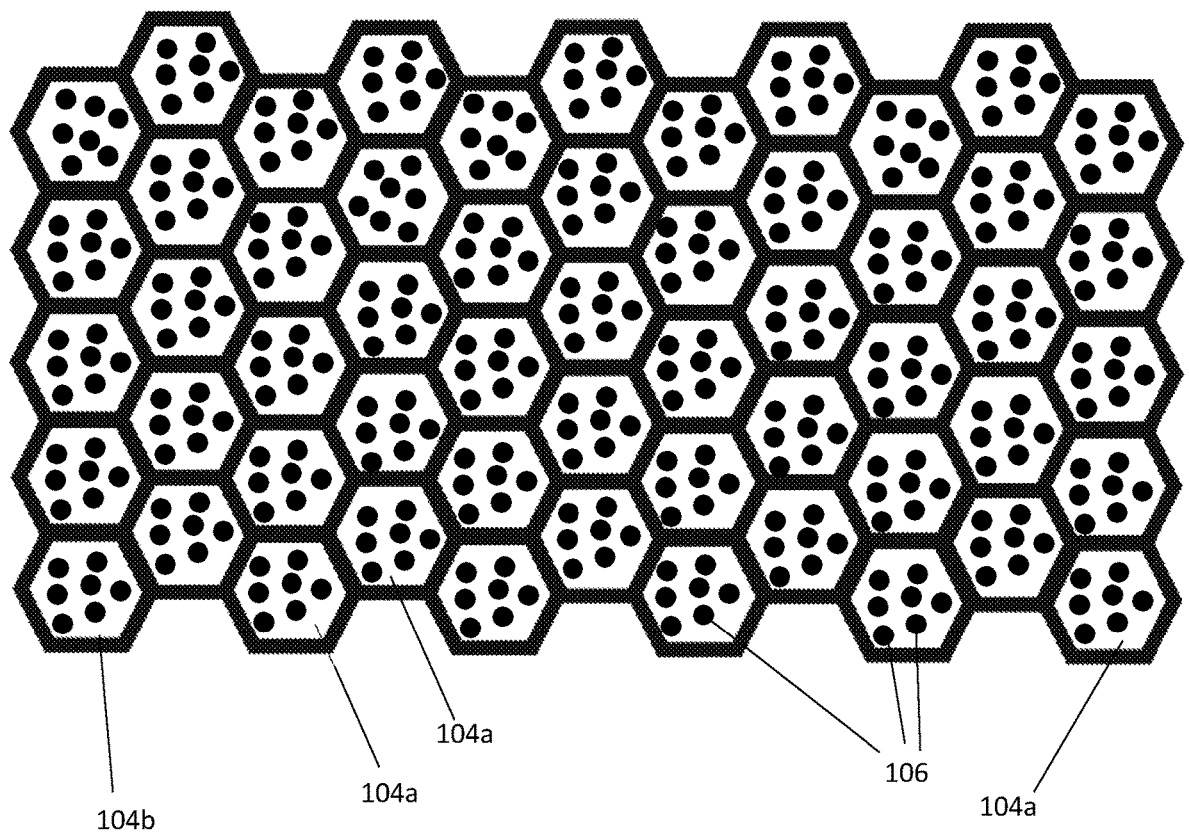
FIG. 2 is a top view of a perforated layer having a plurality of cells for holding beads, according to some embodiments of the present invention.

FIG. 2 is a top view of the perforated layer 104 having a plurality of cells 104a for holding beads 106, according to some embodiments of the present invention.

As mentioned above, the perforated layer 104 includes cells 104a. When the beads 106 are spread on the perforated layer over the top of the lower layer 102 of blanket material, each cell 104a contains about the same number of beads. The divider material 104b between the cells 104a prevents the beads 106 from rolling from one cell to the other, while the lower layer 102 and the perforated layer 104 are disposed horizontally. This ensures that the same number of beads 106 is housed within each cell 104a of the perforated layer 104. Thus, the perforated layer helps maintain a substantially uniform distribution of beads 106 over the lower layer 102.

The divider material 104b may be any material compliant material that can be sewn therethrough. In some embodiments of the present invention, the divider material 104b includes elastic fabric. The cells 104a may have various shapes such as hexagon (honeycomb), square, circle, heart, or rectangle, as long as all of the cells 104a have the same shape.

In some embodiments of the present invention, each cell is a hexagon having a side of 0.25-10 inches. The number of beads 106 contained in each cell depends on the size and weight of the beads and the desired weight distribution over the blanket. In a non-limiting example, each bead 106 is a sphere having a diameter of 0.1-50 millimeters and a mass of 0.01-50 grams. According to a non-limiting example, each hexagonal cell contains 5-5000 such beads. It should be noted that a level of error 25% is permitted in the distribution of the beads.

The beads may be made of silica or lead-free glass. In some embodiment of the present invention, the beads are non-toxic, hypoallergenic, and odorless.

Figure 3:
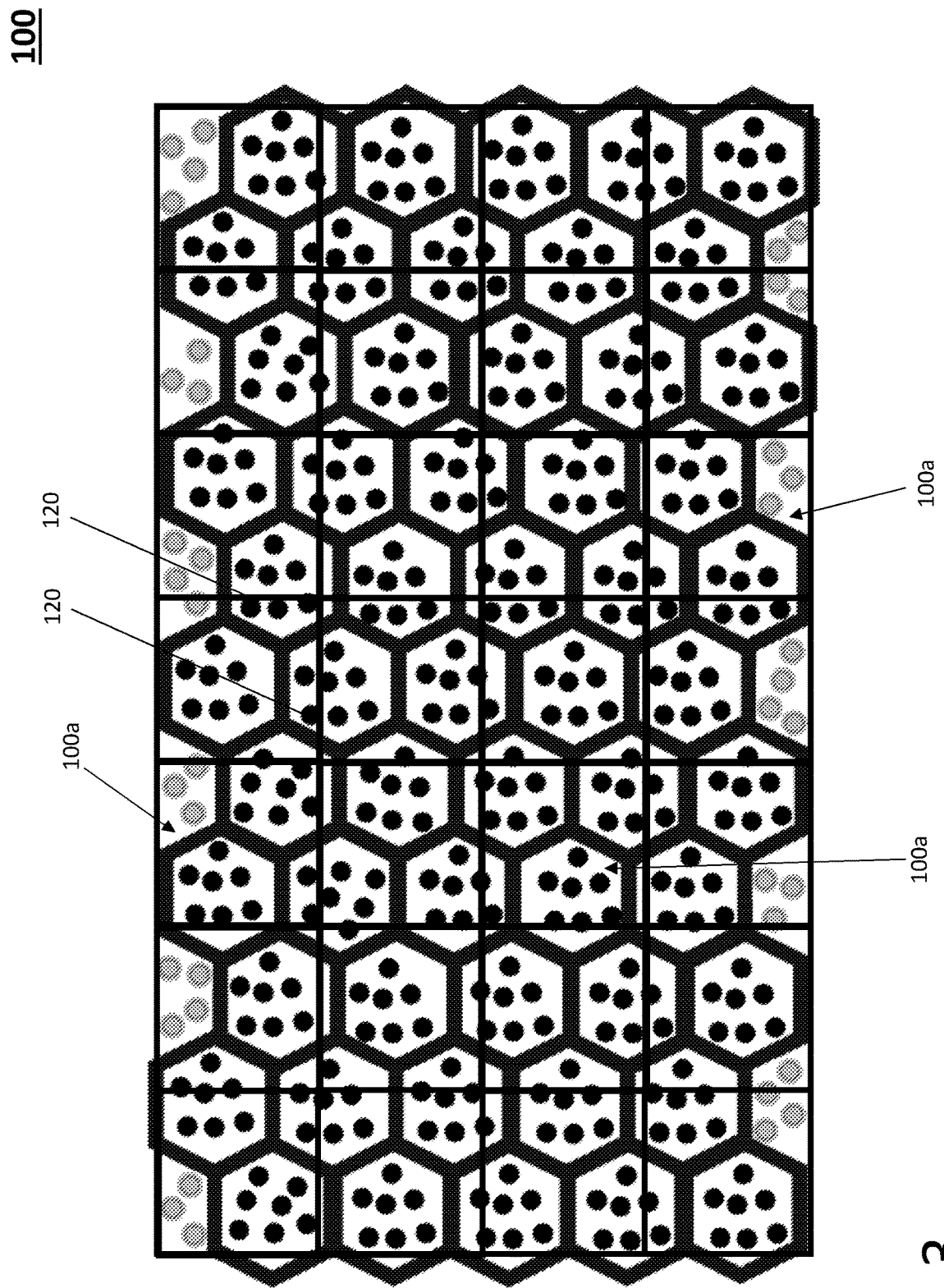
FIG. 3 is a top view of the blanket of the present invention, illustrating the division of the blanket into substantially equal sections, each of which contains a substantially equal number of beads.

FIG. 3 is a top view of the blanket 100 of the present invention, illustrating the division of the blanket 100 into substantially equal sections 100a, each of which contains a substantially equal number of beads 106.

The uniform distribution of beads 106 over the lower layer of blanket material is maintained by the perforated layer 104 until the different units are sewn together. After the sewing occurs along the sewing lines 120, and the blanket 100 is moved around, it is possible that beads 106 may leave the cells 104a, as the blanket may be turned, or the divider material between cells may bend. However, because the beads were uniformly distributed over the lower before and the sewing and because the beads 106 cannot traverse the sewing lines 120 to move between different sections 100a (which have substantially equal shape and surface area), the sections 100a contain substantially the same amount of beads 106. The sections 100a may be square, rectangular, or any other shape.

In a non-limiting example, each section 100a is a square having a side of 0.25-10 inches and contains 5-5000 beads having a diameter of 0.1-20.0 millimeters and a mass of 0.01-10.0 grams. In one embodiment, a level of error of 25% is acceptable in the distribution of the beads, such that the number of beads 106 in each section 100a is the desired number plus or minus 25%.

Figure 4:
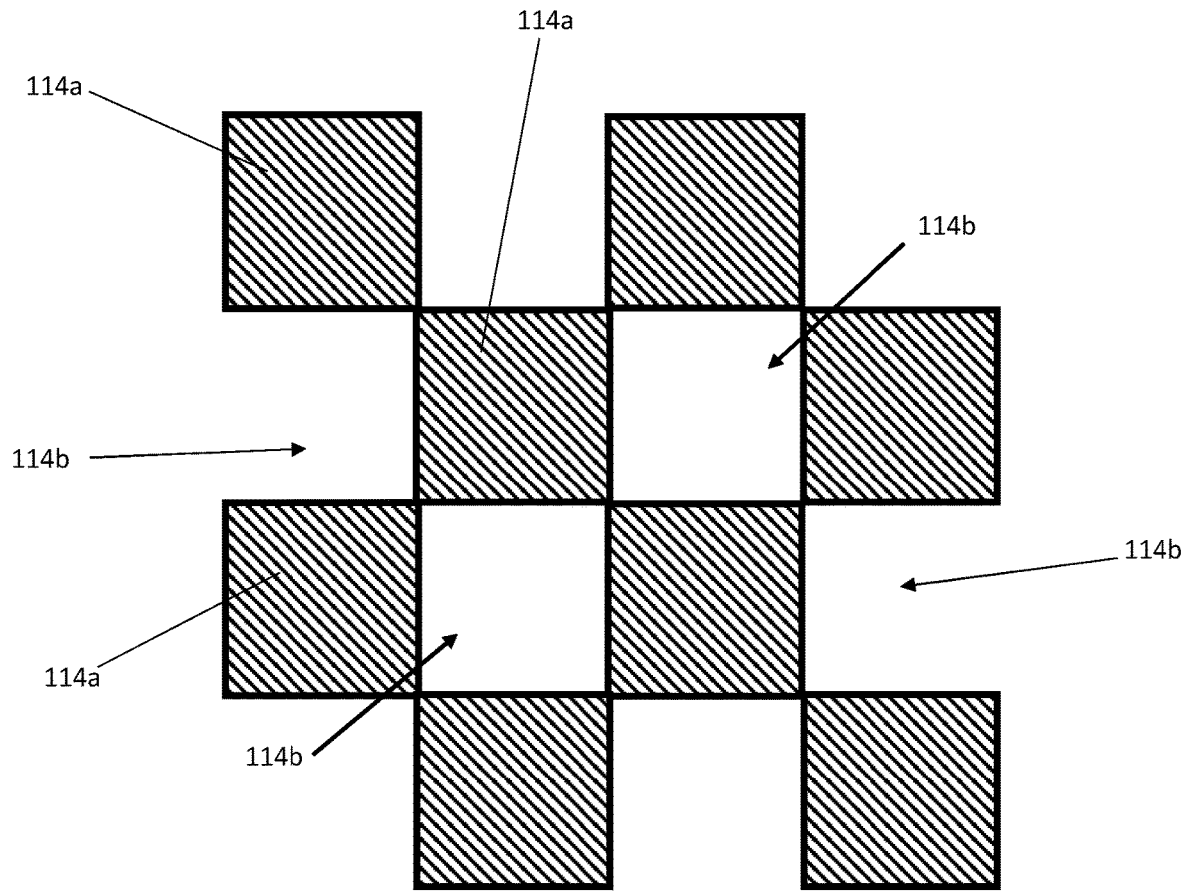
FIG. 4 is a top view of the lattice matrix, illustrating shaped and sized units of fabric alternating with similarly shaped and sized holes, according to some embodiments of the present invention.
Figure 5:
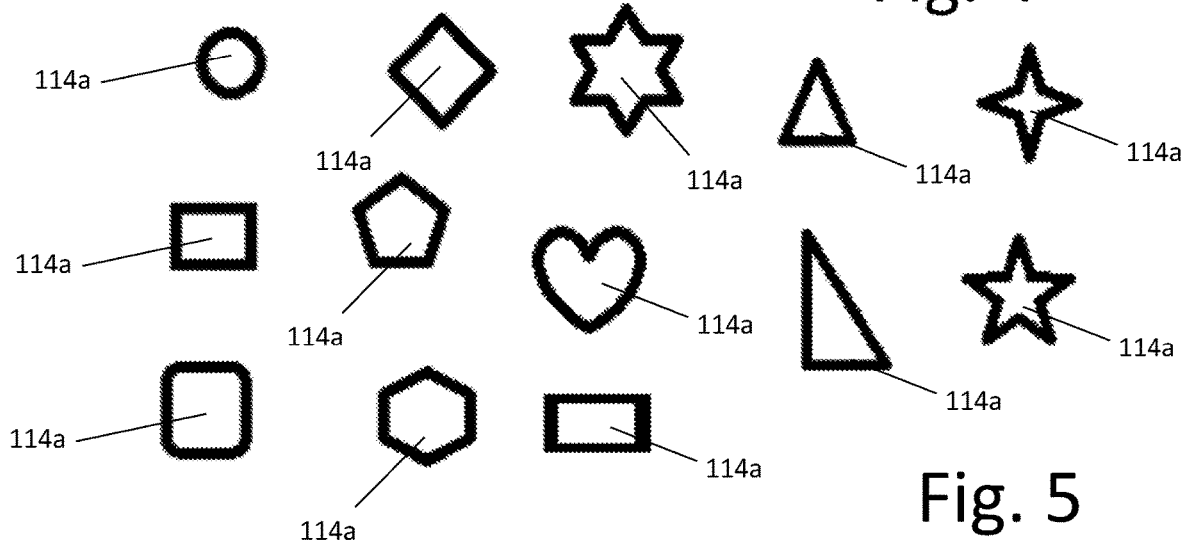
FIG. 5 illustrates different examples of shapes of the units of fabric.

FIG. 4 is a top view of the lattice matrix 114, illustrating shaped and sized units of fabric 114a alternating with similarly shaped and sized holes 114b, according to some embodiments of the present invention. FIG. 5 illustrates different examples of shapes of the units of fabric 114a.

The lattice matrix 114 is flexible in a finite number of directions, but resists bending outside those directions. For example, if the units of fabric 114a and the holes 114b are square, the lattice matrix 114 is flexible along the sides of the squares, but resists bending in a diagonal direction. This enables the lattice matrix 114 to retain its shape, thereby causing the blanket 100 to retain its shape, while maintaining a level of flexibility needed for comfort. It is important that the blanket 100 retains its shape to make sure that the beads 106 are uniformly spread over the user while the user is sleeping. Referring to FIG. 5, the units of fabric 114a and the holes 114b may have any kind of shape including but not limited to circle, triangle, heart, star, and hexagon.

Figure 6:
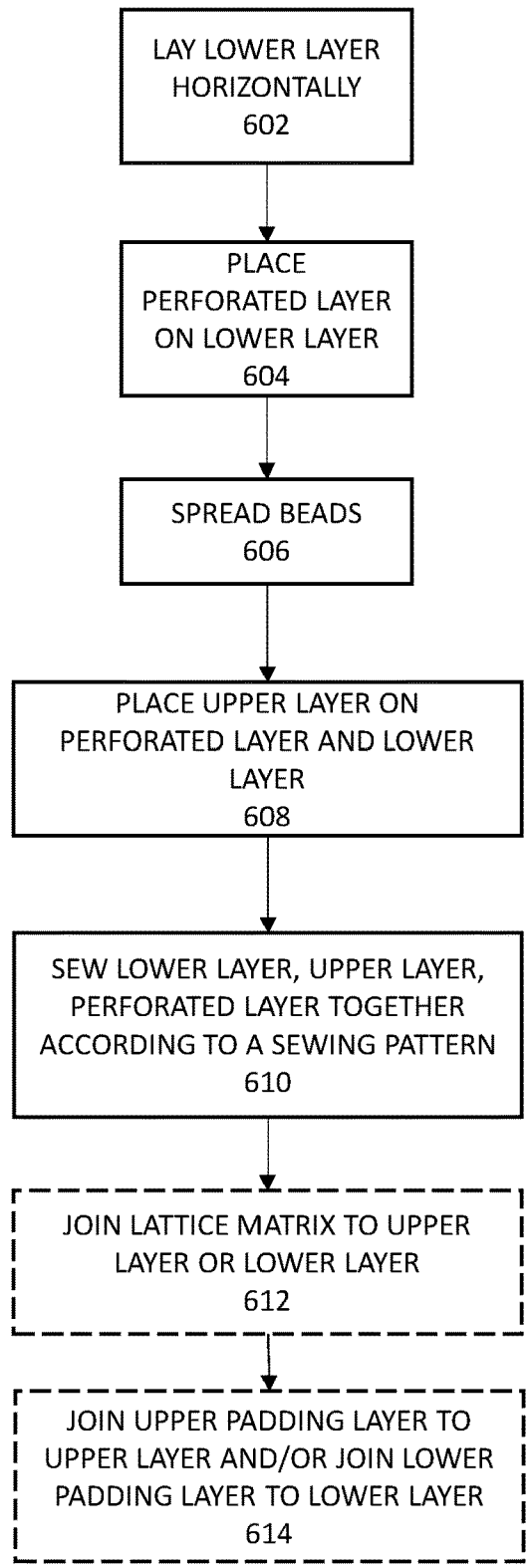
FIG. 6 is a flowchart illustrating a method for manufacturing a weighted blanket, in which the lattice matrix and the padding layers are joined to the upper and/or lower layer of blanket material after the lower layer, upper layer, and perforated layer are sewn together, according to some embodiments of the present invention.

FIG. 6 is a flowchart 600 illustrating a method for manufacturing a weighted blanket, in which the lattice matrix (described above) and the padding layers (described above) are joined to the upper and/or lower layer of blanket material (described above) after the lower layer, upper layer, and perforated layer (described above) are sewn together, according to some embodiments of the present invention.

At 602, the lower layer of blanket material described above is laid horizontally. At 604, the perforated layer described above is placed on top of the lower layer of blanket material.

At 606, the beads (described above) are spread substantially uniformly on a top of the lower layer of blanket material, such that each cell of the perforated layer contains substantially the same amount of beads (plus or minus a certain error, as explained above). The dividing material of perforated layer prevents the beads from leaving the respective cells.

At 608, the upper layer of blanket material described above is placed on a top of the lower layer, such that the lower layer and the upper layer sandwich the perforated layer and the beads.

At 610, the lower layer, upper layer, and the perforated layer are sewn together according to a sewing pattern which divides the blanket into a plurality of substantially equal sections. Each section contains substantially a same amount of beads and that the beads in any of the sections are prevented from crossing between sections 100a. In this manner, a substantially uniform distribution of the beads is maintained over the blanket.

In some embodiments of the present invention, at 612, the lattice matrix described above is joined to the upper layer of blanket material or lower layer of blanket material.

In some embodiments of the present invention, at 614, the upper padding layer described above is joined to the top of the upper layer of blanket material. In some embodiments of the present invention, the lower padding layer described above is joined to the bottom of the lower layer of blanket material.

Figure 7:
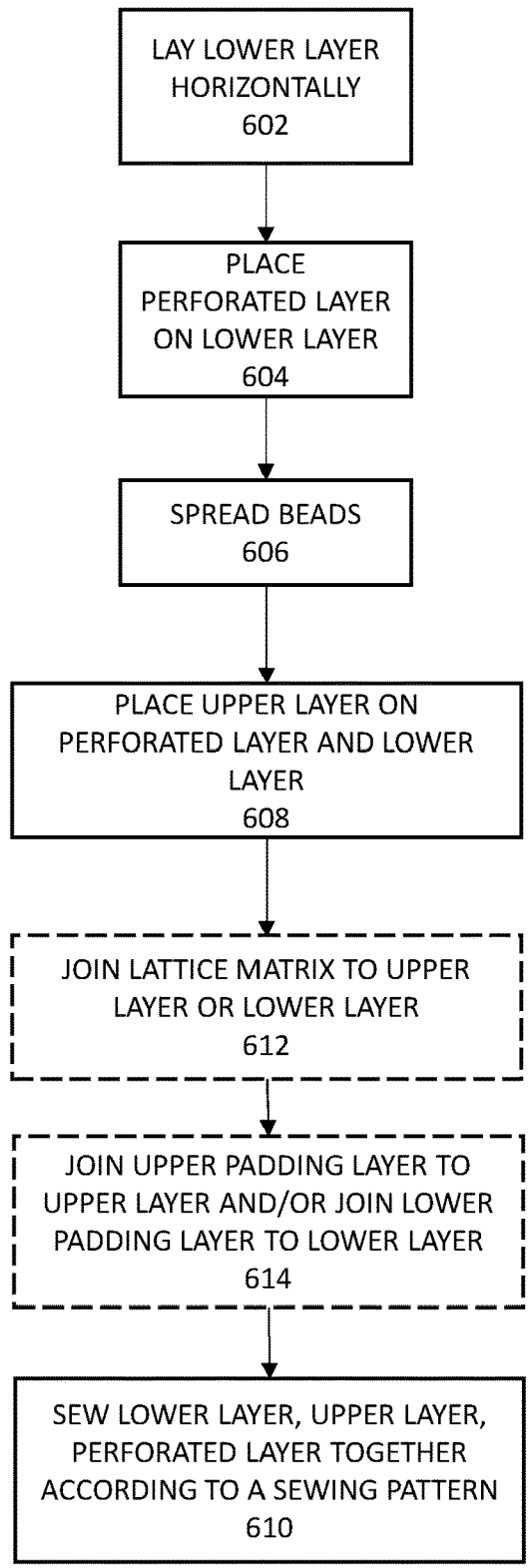
FIG. 7 is a flowchart illustrating a method for manufacturing a weighted blanket, in which the lattice matrix and the padding layers are joined to the upper and/or lower layer of blanket material before the lower layer, upper layer, and perforated layer are sewn together, according to some embodiments of the present invention.

FIG. 7 is a flowchart 700 illustrating a method for manufacturing a weighted blanket, in which the lattice matrix (if present) and the padding layers (if present) are joined to the upper and/or lower layer of blanket material before the lower layer, upper layer, and perforated layer are sewn together, according to some embodiments of the present invention.

The optional steps 612 and 614, if present, occur before the sewing is performed. In this manner, all the units, including the padding layers and lattice matrix 114 are sewn together at once.

What is claimed is:

1. A weighted blanket, comprising:
   a lower layer of blanket material;
   a perforated layer having a plurality of similarly shaped and sized apertures, each aperture defining a cell, the perforated layer being disposed above the lower layer;
   a plurality of beads distributed over the lower layer;
   an upper layer of blanket material disposed above the lower layer of blanket material, such that the lower level and the upper level sandwich the perforated layer and the beads;
   a lattice matrix disposed parallel to the layers of blanket material and joined to at least one of the layers of blanket material, the lattice comprising a pattern of shaped holes alternating with similarly shaped and sized units of fabric, the fabric being at least semi-rigid, such that lattice matrix is configured to be flexible while retaining a shape of the blanket,
   wherein the lower layer, the upper layer, and the perforated layer are sewn together in a sewing pattern that divides the weighted blanket into a plurality of substantially equal sections, such that beads in any of the sections are prevented from crossing into any other one of the sections; and
   wherein prior to the sewing of the lower layer, the upper layer, and the perforated layer, the beads are distributed substantially uniformly over the lower layer of blanket material such that each cell contains substantially a same number of beads and the perforated layer prevents the beads from leaving the respective cell, thereby ensuring that once the lower layer, the upper layer, and the perforated layer are sewn together, each section contains substantially a same amount of beads, thereby ensuring a substantially uniform distribution of beads over the blanket.

2. The blanket of claim 1, comprising at least one of: an upper padding layer disposed above the upper layer of blanket material, and a lower padding layer is disposed below the lower layer of blanket material.

3. The blanket of claim 2, comprising at least one tie loop joined to at least one edge of the upper padding layer or the lower padding layer and being configured to attach to an external structure.

4. The blanket of claim 1, wherein the sections are rectangular or square.

5. The blanket of claim 2, wherein the upper padding layer and/or the lower padding layer comprises preshrunk cotton fabric.

6. The blanket of claim 1, wherein the lower layer of blanket material and/or the upper layer of blanket material comprises polyfill.

7. The blanket of claim 1, wherein the cells of the perforated layer are honeycomb shaped.

8. The blanket of claim 1, wherein the perforated layer comprises elastic fabric.

9. A method for manufacturing a blanket, comprising:
   providing a lower layer of blanket material as a foundation;
   laying the lower layer of blanket material horizontally;
   placing a perforated layer on the lower layer, the perforated layer having a plurality of similarly shaped and sized apertures, each aperture defining a cell, above the lower layer;
   spreading a plurality of beads substantially uniformly on a top of the lower layer with the cells above the lower blanket layer, such that each cell contains substantially a same amount of beads, the perforated layer preventing the beads from leaving the respective cells;
   placing an upper layer of blanket material on a top of the lower layer such that the lower layer and the upper layer sandwich the perforated layer and the beads;
   sewing the lower layer, upper layer, and the perforated layer together according to a sewing pattern which divides the blanket into a plurality of substantially equal sections, such that each section contains substantially a same amount of beads and that the beads in any of the sections are prevented from crossing between sections, thereby maintaining a substantially uniform distribution of the beads over the blanket;
   joining a lattice matrix to at least one of the upper layer and the lower layer, such that the lattice matrix is disposed parallel to the upper layer and the lower layer, the lattice matrix having a pattern of a shaped holes alternating with similarly shaped and sized units of fabric, the fabric being at least semi-rigid, such that lattice matrix is configured to be flexible while retaining a shape of the blanket.

10. The method of claim 9, further comprising at least one of:
    joining an upper padding layer to a top of the upper layer of blanket material; and
    joining a lower padding layer to a bottom of the lower layer of blanket material.

11. The method of claim 10, further comprising joining at least one tie loop to at least one edge of the upper padding layer or of the lower padding layer, the at least one tie loop being configured to attach to an external structure.

12. The method of claim 9, wherein the substantially equal sections are square or rectangular.

13. The method of claim 10, wherein the upper padding layer and/or the lower padding layer comprise preshrunk cotton fabric.

14. The method of claim 9, wherein the lower layer of blanket material and/or the upper layer of blanket material comprise polyfill.

15. The method of claim 9, wherein the cells of the perforated layer that are honeycomb shaped.

16. The method of claim 9, wherein the perforated layer comprises elastic fabric.

* * * * *